(12) United States Patent
Chen et al.

(10) Patent No.: US 8,138,363 B2
(45) Date of Patent: Mar. 20, 2012

(54) PROCESS FOR THE PRODUCTION OF ALKANOLAMIDE

(75) Inventors: Xin Chen, Hockessin, DE (US); Howard W. Prokop, Chadds Ford, PA (US); Stephen Howard Colmery, Newark, DE (US)

(73) Assignee: Uniqema Americas LLC, Wilmington, DE (US)

( * ) Notice: Subject to any disclaimer, the term of this patent is extended or adjusted under 35 U.S.C. 154(b) by 48 days.

(21) Appl. No.: 12/312,293

(22) PCT Filed: Nov. 2, 2007

(86) PCT No.: PCT/US2007/023210
§ 371 (c)(1),
(2), (4) Date: Dec. 4, 2009

(87) PCT Pub. No.: WO2008/057455
PCT Pub. Date: May 15, 2008

(65) Prior Publication Data
US 2010/0121086 A1    May 13, 2010

Related U.S. Application Data

(60) Provisional application No. 60/856,797, filed on Nov. 6, 2006.

(51) Int. Cl.
*C07C 231/00* (2006.01)

(52) U.S. Cl. ......................................................... 554/69

(58) Field of Classification Search ..................... 554/69
See application file for complete search history.

(56) References Cited

U.S. PATENT DOCUMENTS

| 2,089,212 A |   | 8/1937 | Kritchevsky | |
| 2,844,609 A | * | 7/1958 | Tesoro ............................. | 554/66 |
| 4,330,339 A | * | 5/1982 | Nimerick ...................... | 106/243 |

FOREIGN PATENT DOCUMENTS

JP    2000273073 A    10/2000

OTHER PUBLICATIONS

International Search Report dated Feb. 28, 2008 for PCT/US2007/023210.
European Search Report dated Aug. 5, 2010 for corresponding European Application No. 07861678.
Kroll, Harry et al. "The Chemistry of Lauric Acid-Diethanolamine Condensation Products," *Journal of the American Oil Chemists' Society*, 34 (Jun. 30, 1957) 323-326.
Smith, John R. Lindsay et al. "The Reactions of Amine, Polyamine and Amino Alcohol Corrosion Inhibitors in Water at High Temperature," *J. Chem, Soc. Perkin Trans* 2, 6 (Jan. 1, 1992) 939-947.

* cited by examiner

*Primary Examiner* — Deborah D Carr
(74) *Attorney, Agent, or Firm* — Jones Day

(57) ABSTRACT

The present invention relates to a process for the manufacture of alkanolamide containing compositions, and more particularly to a process of reacting a fatty acid and diethanolamine (DEA) which result in the formation of low levels of undesirable by products, particularly of bis-hydroxyethyl piperazine (BHEP).

22 Claims, No Drawings

PROCESS FOR THE PRODUCTION OF ALKANOLAMIDE

CROSS REFERENCE TO RELATED APPLICATIONS

This application is the National Phase application of International Application No. PCT/US2007/023210, filed Nov. 2, 2007, which designates the United States and was published in English, and which further claims the benefit of priority from U.S. Provisional Application No. 60/856,797, filed Nov. 6, 2006. These applications, in their entirety, are incorporated herein by reference.

FIELD OF INVENTION

The present invention relates to a process for the manufacture of alkanolamide containing compositions, and more particularly a process of reacting a fatty acid and diethanolamine (DEA) which results in the formation of low levels of undesirable by-products.

BACKGROUND OF THE INVENTION

There is a significant problem with existing methods of manufacture of alkanolamides and the by-products formed thereby. It has been found that by-products are prone to form throughout the reaction process. A particularly significant impurity, bis-hydroxyethyl piperazine (BHEP), is formed via dimerisation of two DEA molecules. BHEP crystallizes out of the composition, particularly if present in concentrations of over 5000 ppm, though lower concentrations may also be problematic in some circumstances. Crystallisation of BHEP out of the composition may result in an end user perceiving problems with the composition as deposits of BHEP appearing in, for example, barrels of the composition would give the appearance of a contaminated or faulty batch, even if there would be no deleterious effects of the BHEP in use. Thus the effects of significant BHEP presence in an alkanolamide composition make it an undesirable constituent.

Accordingly, it is desirable to provide improved methods of production of such an alkanolamide, which contain a reduced amount of undesirable reaction by-products, particularly BHEP.

SUMMARY OF THE INVENTION

According to the present invention there is provided a method of manufacture of a composition comprising an alkanolamide, the method comprising the steps of:
a) adding DEA to a fatty acid at a low addition rate to form a mixture of fatty acid and DEA wherein the total molar quantity of fatty acid in the mixture is in excess of the total molar quantity of DEA in the mixture;
b) applying at least a partial vacuum to the mixture; and
c) maintaining the mixture at a suitable temperature and for sufficient time for the reaction to proceed to form the alkanolamide.

The reaction should generally proceed to form the alkanolamide at a desired quality. Typically this is achieved when the DEA quantity has decreased to an acceptable level, e.g. 2% or less, preferably 1% or less. The concentration of DEA can be measured by any suitable analytical technique, and gas chromatography, as herein described, is preferred.

A low rate of addition of DEA, the non-stoichiometric conditions (i.e. excess fatty acid) and/or application of reduced pressure have been found to reduce the rate of production and/or total amount of BHEP. Use of such reaction parameters means that levels of BHEP significantly below 5000 ppm can be achieved. Optimisation of the method means that BHEP levels of 3000 ppm or below are easily achievable. In general it is desirable to reduce BHEP levels as far as possible, but the disadvantages of a slight BHEP level must be balanced with the efficiency of the process overall. BHEP levels of 3000 ppm or below are in many cases satisfactory as the tendency of BHEP to crystallise out of the composition is significantly reduced or removed at such levels. However, compositions containing BHEP at levels of 2000 ppm or below are desirable in certain circumstances. The concentration of BHEP can be measured by any suitable analytical technique, and gas chromatography, as herein described, is preferred.

Suitably the total amount of fatty acid with respect to DEA is in the range of molar ratios of about 1:0.4-0.9 (fatty acid:DEA), preferably in the range of about 1:0.5-0.85, more preferably about 1:0.6-0.8, particularly about 1:0.7.

Suitable addition rates for DEA are from about 0.0001% of total DEA per minute to about 10% total DEA per minute, preferably from about 0.001% to about 5%, more preferably from about 0.001% to about 1%, particularly from about 0.002% to about 0.5%. In general a slower addition rate is preferred in order to minimise BHEP accumulation, but this must be balanced against drawing the time taken to produce a batch of the composition out to an unacceptable or uneconomic duration.

In one embodiment of the present invention, both the addition of DEA to the fatty acid and the reaction (i.e. the time at reaction temperature) are conducted under a vacuum. However, in some embodiments it may be satisfactory if the addition of DEA is not conducted under a vacuum, or may be at a lesser vacuum than the reaction. Suitably the vacuum is an absolute pressure of 500 mm Hg (absolute pressure) or lower, preferably 250 mm Hg or lower, more preferably 125 mm Hg or lower especially 50 mm Hg or lower. In general a greater (deeper) vacuum is preferable in terms of accelerating the reaction process and limiting BHEP production. However, it may be desirable to reduce the vacuum (i.e. increase the pressure) during the addition of the DEA or at other points during the reaction to reduce foaming. Suitably the vacuum is maintained for a substantial portion of the reaction, preferably for essentially the entire time of the reaction. Preferably the vacuum is maintained for substantially the entire time of the reaction and substantially the entire time of addition of the DEA to the fatty acid.

Suitably the reaction is conducted at a temperature of from about 100° C. to about 170° C., preferably from about 125° C. to about 160° C., more preferably from about 145° C. to about 155° C., particularly from about 148° C. to about 152° C. It is preferred that this temperature is maintained for substantially the entire time of the reaction.

It is preferred that the reaction proceeds for not longer than 16 hours, preferably 12 hours or less, more preferably 8 hours or less, especially 6 hours or less. If the reaction proceeds for longer than 16 hours an excessive build up of BHEP is generally observed. The time of the reaction proceeding is generally taken to be the time for which the temperature is maintained at the desired reaction temperature (i.e. in a preferred embodiment, at between 148° C. to 152° C.). In general the DEA is added to the fatty acid at a temperature below the reaction temperature, typically around 135° C. to 140° C. The heat produced by the exothermic reaction between DEA and fatty acid can then be used to raise the temperature to the reaction temperature. It is of course possible to cool the mixture or provide additional heat to maintain the reaction at the desired temperature. Thus the time of the reaction may in many cases be taken to run from the end of the addition of DEA until the time when the reaction is stopped, i.e. allowed to cool.

The term fatty acid as used herein refers to fatty acids and derivatives thereof, e.g. fatty acid esters such as the methyl, ethyl and/or isopropyl esters, or fatty acid mono-, di- and triglycerides. The term fatty acid can include a mixture of two or more fatty acids and/or derivatives thereof.

Preferred fatty acids for use in the present invention suitably comprise from 8 to 24, preferably from 10 to 22, more preferably from 12 to 20, and particularly from 12 to 18 carbon atoms.

Suitable fatty acids can be obtained from natural sources such as, for instance, plant or animal esters (e.g. palm oil, rape seed oil, palm kernel oil, coconut oil, babassu oil, soybean oil, castor oil, tallow, whale or fish oils, grease, lard, and mixtures thereof). The fatty acids can also be synthetically prepared, for example as described in "Fatty Acids in Industry", Ed. Robert W Johnson, Earl Fritz, Marcel Dekker Inc, 1989 ISBN 0-8247-7672-0.

Accordingly, suitably fatty acids include cocoate, capric, lauric, myristic, palmitic, stearic, oleic, linoleic, arachidonic, erucic and/or behenic acids or a mixture of two or more thereof. Specific branched chain fatty acids suitable for use in the present invention include iso-acids such as isostearic acid, isopalmitic acid, isomyristic acid, isoarachidic and isobehenic acid; neo acids such as neodecanoic acid; and other acids such as 2-ethyl hexanoic acids. Particularly suitable branched chain fatty acids contain alkyl side branches (attached directly to a carbon atom of the longest linear chain) having on average less than 5, preferably less than 3, more particularly in the range of 1.05 to 2, especially 1.1 to 1.5 carbon atoms, i.e. the side branches are predominantly methyl groups.

A particularly preferred fatty acid for use in the present invention is isostearic acid (ISAC), such as commercially available materials Prisorine™ 3501, 3502, 3503 or 3505 (ex Uniqema).

To achieve particularly low levels of BHEP it is preferred that the reaction is conducted at as low a pressure as possible, the DEA is added as slowly as possible, the temperature is maintained at between 148° C. to 152° C. for the duration of the reaction and that the reaction is not allowed to proceed beyond 16 hours. Each of these conditions is believed to have a role in accelerating progress of the reaction and/or limiting accumulation of BHEP. Accordingly, the best results would be obtained where all the above conditions are applied and optimised, but satisfactory results may be obtained without all of the above conditions being applied, or where one or more of them is not optimised.

In a further embodiment the process of the present invention comprises the following steps:
(a) sampling the mixture as the reaction progresses;
(b) determining the acid number of the sample; and
(c) halting the reaction once the acid number drops to 1.2, or halting the reaction once the acid number is below 2 and the acid number does not vary by greater than 0.1 from a previous sample.

Suitably the previous sample is taken from 20 minutes to 2 hours previously, preferably from 40 minutes to 1 hour and 20 minutes previously, and conveniently about 1 hour previously.

According to a further aspect, the present invention provides a composition which is the product of a method described herein comprising an alkanolamide which comprises less than 5000 ppm of BHEP. In a preferred embodiment the composition comprises less than 3000 ppm, especially less than 2000 ppm of BHEP.

The alkanolamide composition suitably has the following physical properties:
Appearance: Clear amber, viscous liquid
Acid number (mg KOH/g): 2.0 max
Alkali value (kg KOH/g): 30 max
DEA Content (%): 1.0 max
Flash point, ° F. (PMCC): 220 min
BHEP content: <5000 ppm
Water content: 0.1 max Of these properties the most significant are BHEP content and DEA content, and the other physical properties are indicators of particular suitability. Accordingly, in one embodiment of the present invention the composition has BHEP content of <5000 ppm and a DEA content of $\leq$1%.

Embodiments of the present invention will now be described by way of example only. It should be noted that the described embodiments do not limit the scope of the invention.

Example of Composition Production Process

An example of a process for manufacturing a composition in accordance with the present invention involves a reaction producing a DEA amide (i.e. an alkanolamide). The reaction of fatty acid and diethanolamine (DEA) forms DEA amides and water. The by-product water can be removed by vacuum stripping, i.e. distillation.

During the reaction to form the alkanolamide from a fatty acid and DEA, it has been observed that an impurity that is a derivative of piperazine, bis-hydroxyethyl piperazine (BHEP), forms over the course of the reaction. BHEP can precipitate out of the reaction product over time, particularly at concentration over 5000 ppm so it is essential to keep this by-product under control. The formation of this undesirable by-product presents a significant problem in the manufacture of alkanolamides. To limit the level of this impurity, a number of steps are taken during the manufacturing process.

The time at temperature (i.e. reaction time) for this reaction is generally limited to 16 hours and preferably significantly less. Running the reaction beyond 16 hours causes a build up of BHEP and should thus generally be avoided.

It should be noted that this reaction provides an exception to the general trend of alkali number drift in other related products. The alkali number of the product of this reaction generally remains stable because of reaction conditions that leave virtually no free DEA in the product.

An exemplary reaction process can be summarised as follows:

The diethanolamine (DEA) was kept molten by maintaining at 38±5.5° C. (100±10° F.).

The reactor was set up ready to receive the reactants (a suitable reactor is a R3200 reactor).

The reactor was charged with the fatty acid, i.e. isostearic acid (e.g. isostearic available under trade name Prisorine™ 3501, 3502, 3503 or 3505 (ex Uniqema)). The isostearic acid was added at the maximum rate for the particular reactor. Obviously, the amount of reactants will be changed to suit the volume of the particular reactor, whilst maintaining the desired ratio of reactants.

The agitator was set to run at a suitable rate to achieve satisfactory mixing of the mixture.

The reactor was heated to 138° C. (280° F.). The reactor heater was then switched off. The exothermic reaction of the fatty acid and DEA elevated the temperature to the desired level for the reaction.

The reactor was charged with DEA, to give a molar ratio of 1:0.7 (isostearic acid:DEA). The DEA was added slowly, i.e. at a rate of around 25 lbs/min for a total DEA load of 7690 lbs (3488 kg)—which corresponded to an isostearic acid load of 32310 lbs (14656 kg).

The reaction was heated to 149° C. (300° F.) at rate of 0.8° C./min (1.5° F./min) and the water distillation was started. The heating was generally provided by the exothermic reaction between the fatty acid and DEA, but additional heating or cooling can be provided if required to achieve and/or maintain the desired temperature. Excessive foam build up at the beginning of distillation was watched for.

When the temperature reached 149° C. (300° F.) the time was recorded. This was used to track the total time at temperature for the batch (i.e. "reaction time").

The reactor was held at 149° C. (300° F.) and the vacuum was brought down to the desired level (e.g. below 50 mm Hg). It was important to observe for excessive foam build up at the beginning of vacuum ramp.

Once full vacuum had been reached, the conditions were held. The temperature was not allowed to exceed 153° C. (307.5° F.).

The mixture within the reactor was sampled regularly to check reaction progress (e.g. hourly).

When each sample was taken the total time for the batch at 149° C. (300° F.) was recorded. The results of the sample analysis were logged. Suitable acid and alkali number end parameters for the reaction product were:

Acid Number: 2.0 max
Alkali Number: 30 max

Each sample was compared with the following parameters to determine if the reaction end point had been reached. If one of the three batch parameters was met then the next step in the process was proceeded to. If none of the three following parameters were met, the reaction conditions were maintained and the batch re-sampled later. There were, in general no running adjustments to the batch. The reaction parameters used to mark the end point were as follows:

a) the acid number was 1.2 or less;
b) the acid number was 2.0 or less and within 0.1 units of the acid number of the previous sample; or
c) the total time for the batch at 149° C. (300° F.) reached 16 hours.

Once one of the three criteria above had been met, the mixture was cooled and the vacuum was broken.

The reaction mixture was again sampled to check the final batch properties and the results logged. The results were within the following parameters:

Gardner Color: 5 max
Acid no.: 2.0 max
Alkali no.: 30 max
Water (%): 0.1 max

When the batch was within specification, the reaction product was then transferred from the reactor to barrels or other containers as appropriate.

Such a method as described above was capable of producing an alkanolamide containing composition with a BHEP content of less than 3000 ppm. The concentration of BHEP was measured by gas chromatography using an Agilent Model 6890 equipped with a split/split-less injector, a 7683 autosampler and a flame ionization detector. The sample was dissolved in pyridine in the presence of an internal standard and then derivatized and analysed by gas chromatography.

It may be possible that further optimisation of the process may result in even lower levels of BHEP, and such an optimised process is within the scope of the present invention.

COMPARATIVE EXAMPLE

As a control reaction the process described above was repeated with the following differences:

A stoichiometric mixture of DEA and isostearic acid was used (i.e. a 1:1 molar ratio).
The DEA was not added slowly, but rather at the maximum rate achievable with the reactor.

Otherwise the reaction conditions were identical.

The product of this reaction typically contained at least 6000 ppm BHEP. When the product was stored in barrels for a period of two weeks, significant deposits of BHEP developed on the sides of the barrel. The example of the invention did not develop such deposits.

Modifications to the described examples may be made without departing from the scope of the present invention.

What is claimed is:

1. A method of manufacture of a composition comprising an alkanolamide, the method comprising the steps of:
    (a) adding diethanolamine (DEA) to a fatty acid at a low addition rate to form a mixture of fatty acid and DEA wherein the total molar quantity of fatty acid in the mixture is in excess of the total molar quantity of DEA;
    (b) applying at least a partial vacuum to the mixture; and
    (c) maintaining the mixture at a suitable temperature and for sufficient time for the reaction to proceed to form the alkanolamide.

2. The method of claim 1 wherein the fatty acid is selected from the group consisting of cocoate, capric, lauric, myristic, palmitic, stearic, oleic, linoleic, arachidonic, erucic and behenic acids and mixtures thereof.

3. The method of claim 1 wherein the fatty acid comprises isostearic acid.

4. The method of claim 1 wherein the fatty acid consists of isostearic acid.

5. The method of claim 1 wherein the DEA is added at a rate of from about 0.0001% to about 10% of total DEA per minute.

6. The method of claim 5 wherein the DEA is added at a rate of from about 0.001% to about 5% of total DEA per minute.

7. The method of claim 6 wherein the DEA is added at a rate of from about 0.001 to about 1% of total DEA per minute.

8. The method of claim 7 wherein the DEA is added at a rate of from about 0.002% to about 0.5% total DEA per minute.

9. The method of claim 1 wherein the total amount of fatty acid with respect to DEA is in the range of molar ratios of about 1:0.4-0.9 (fatty acid:DEA).

10. The method of claim 9 wherein the range of molar ratios is about 1:0.5-0.85.

11. The method of claim 10 wherein the range of molar ratios is about 1:0.6-0.8.

12. The method of claim 11 wherein the range of molar ratios is about 1:0.7.

13. The method of claim 1 wherein the mixture is maintained at a pressure of about 500 mm Hg or less for a substantial portion of the time of the reaction.

14. The method of claim 13 wherein the mixture is maintained at a pressure of about 250 mm Hg or less for a substantial portion of the time of the reaction.

15. The method of claim 14 wherein the mixture is maintained at a pressure of about 125 mm Hg or less for a substantial portion of the time of the reaction.

16. The method claim 15 wherein the mixture is maintained at a pressure of about 50 mm Hg or less for a substantial portion of the time of the reaction.

17. The method of claim 13 in which the pressure is maintained for essentially the entire time of the reaction.

18. The method of claim 17 in which the pressure is maintained for essentially the entire time of the reaction and the entire time of the addition of the DEA.

19. The method of claim 1 wherein the mixture is maintained at a temperature of from about 100° C. to about 170° C.

20. The method of claim 19 wherein the mixture is maintained at a temperature of from about 125° C. to about 160° C.

21. The method of claim 20 wherein the mixture is maintained at a temperature of from about 145° C. to about 155° C.

22. The method of claim 21 wherein the mixture is maintained at a temperature of from about 148° C. to about 152° C.

* * * * *